(12) United States Patent
Liu et al.

(10) Patent No.: US 10,526,271 B2
(45) Date of Patent: Jan. 7, 2020

(54) COMPOSITIONS AND METHODS RELATED TO HALF SALTS OF HERBICIDAL CARBOXYLIC ACIDS

(71) Applicant: Dow AgroSciences LLC, Indianapolis, IN (US)

(72) Inventors: Lei Liu, Carmel, IN (US); Holger Tank, Indianapolis, IN (US); Melissa Gail Olds, Zionsville, IN (US); Stephen L. Wilson, Zionsville, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 15/378,659

(22) Filed: Mar. 9, 2017

(65) Prior Publication Data

US 2017/0210691 A1  Jul. 27, 2017

Related U.S. Application Data

(60) Provisional application No. 62/266,814, filed on Dec. 14, 2015.

(51) Int. Cl.

| | | |
|---|---|---|
| *C07C 59/31* | (2006.01) | |
| *A01N 37/10* | (2006.01) | |
| *A01N 57/20* | (2006.01) | |
| *C07D 213/64* | (2006.01) | |
| *A01N 39/04* | (2006.01) | |
| *A01N 39/02* | (2006.01) | |
| *A01N 43/40* | (2006.01) | |

(52) U.S. Cl.
CPC .............. *C07C 59/31* (2013.01); *A01N 37/10* (2013.01); *A01N 39/02* (2013.01); *A01N 39/04* (2013.01); *A01N 43/40* (2013.01); *A01N 57/20* (2013.01); *C07D 213/64* (2013.01)

(58) Field of Classification Search
None
See application file for complete search history.

(56) References Cited

U.S. PATENT DOCUMENTS

| | | | |
|---|---|---|---|
| 5,714,157 A * | 2/1998 | Sandell | A01N 25/14 424/405 |
| 2008/0207453 A1 | 8/2008 | Kramer | |
| 2011/0257012 A1* | 10/2011 | Stagg | A01N 33/12 504/128 |
| 2013/0045869 A1 | 2/2013 | Liu | |
| 2015/0196030 A1 | 7/2015 | Degenhardt et al. | |
| 2015/0335016 A1 | 11/2015 | Simon et al. | |

OTHER PUBLICATIONS

A. Lawson, "Getting chemistry in the spray tank right," <https://grdc.com.au/news%ADand%ADmedia/news%ADand%ADmedia%ADreleases/south/2015/01/getting%ADchemistry%ADin%ADthe%ADspray%ADtank%ADright1/5>, published Jan. 28, 2015, p. 1-5.*
A. Lawson, "Getting chemistry in the spray tank right," <https://grdc.com.au.news%ADandmedia/news%ADand%ADmediaa%ADreleases/south/2015/01/getting%ADchemistry%ADin%ADthe%ADspray%%ADtank%ADright1/5>, published Jan. 28, 2015, p. 1-5.

* cited by examiner

*Primary Examiner* — Monica A Shin

(57) ABSTRACT

Half salts of certain synthetic auxin herbicides are provided. These half salts are useful for controlling unwanted plant growth. The half salts have low solubility in water, low volatility relative to commercial compositions of the corresponding synthetic auxin herbicides, and offer comparable herbicidal performance when compared to existing salts of the synthetic auxin herbicides.

43 Claims, 4 Drawing Sheets a)

b)

COMPOSITIONS AND METHODS RELATED TO HALF SALTS OF HERBICIDAL CARBOXYLIC ACIDS

BACKGROUND

Compositions containing herbicidal and plant growth modifying chemicals are widely used in agricultural, industrial, recreational, and residential areas worldwide. The active ingredients of such compositions are frequently carboxylic acids, more particularly their salts. These carboxylic acid salts generally have high water solubility leading to their use in high strength aqueous concentrates intended for dilution in water prior to application by spraying or other means.

Carboxylic acid herbicides such as the synthetic auxin herbicides, e.g., 2,4-dichlorophenoxyacetic acid (2,4-D), have long been used to control unwanted vegetation. 2,4-D is normally provided in liquid formulations as a water soluble amine salt or an emulsifiable ester. In certain circumstances, however, these chemical forms of 2,4-D suffer from problems such as incompatibility with other herbicides or off-target movement because of volatility.

Therefore, there is a need for new herbicide products that offer improved performance, stability/compatibility, and flexibility to the end user.

SUMMARY

Half salts of synthetic auxin herbicides, herbicidal compositions containing the half salt, and methods of use thereof are described herein.

Exemplary half salts of the synthetic auxin herbicides include, but are not limited to, those having the formula:

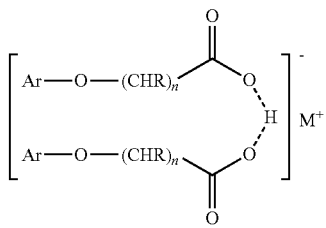

wherein R is independently H or $CH_3$, n is an integer 1, 2 or 3, and Ar is a phenyl or pyridine group substituted with one or more substituents selected from halogen, $C_1$-$C_6$ alkyl, $C_1$-$C_6$ haloalkyl, $C_1$-$C_6$ alkoxy, amino, $C_1$-$C_6$ alkylamino, and di($C_1$-$C_6$ alkyl)amino and M is a cation selected from a metal cation or a tetrasubstitued ammonium cation.

Exemplary synthetic auxin herbicides include, but are not limited to, pyridinyloxyacetic acid herbicides such as fluroxypyr and triclopyr; phenoxyacetic herbicides such as 4-CPA, 2,4-D, 3,4-DA, and MCPA; phenoxybutyric acid herbicides such as 4-CPB, 2,4-DB, 3,4-DB, and MCPB; phenoxypropionic acid herbicides such as cloprop, 4-CPP, dichlorprop, 3,4-DP, fenoprop, mecoprop, and mecoprop-P. In some embodiments the synthetic auxin herbicides include 2,4-D, 2,4-DB, triclopyr, fluroxypyr, MCPA, MCPB, mecoprop, and mecoprop-P Suitable cations include, but are not limited to, monovalent metal cations, such as sodium, potassium, and lithium. Other suitable cations include, but are not limited to, tetrasubstituted ammonium ions such as tetramethyl ammonium, tetraethylammonium, and choline.

The described herbicidal compositions can be prepared as liquid and dry concentrates, which may contain additional inert ingredients, and when mixed with water form spray mixtures that are useful in controlling unwanted vegetation. The described herbicidal compositions also include spray solutions made by adding the liquid or dry concentrates to water.

The half salts and compositions containing the same can be used to control undesirable vegetation in a variety of crops. The half salts and compositions containing the same can be contacted with the undesirable vegetation or a locus thereof, or applied to the soil to prevent the emergence of the undesirable vegetation. The half salts and compositions containing the same exhibit herbicidal activity on an acid equivalent (AE) basis that is comparable to the commercially used synthetic auxin herbicide amine salts.

The half salts described herein may also show improved compatibility with one or more additional herbicides, such as glyphosate and/or glufosinate, exhibit reduced volatility compared to the acid, amine full salt or ester of the corresponding auxin herbicide, and provide reduced soil mobility compared to the full salt or ester of the corresponding auxin herbicide.

DETAILED DESCRIPTION

I. Definitions

Figure 1:
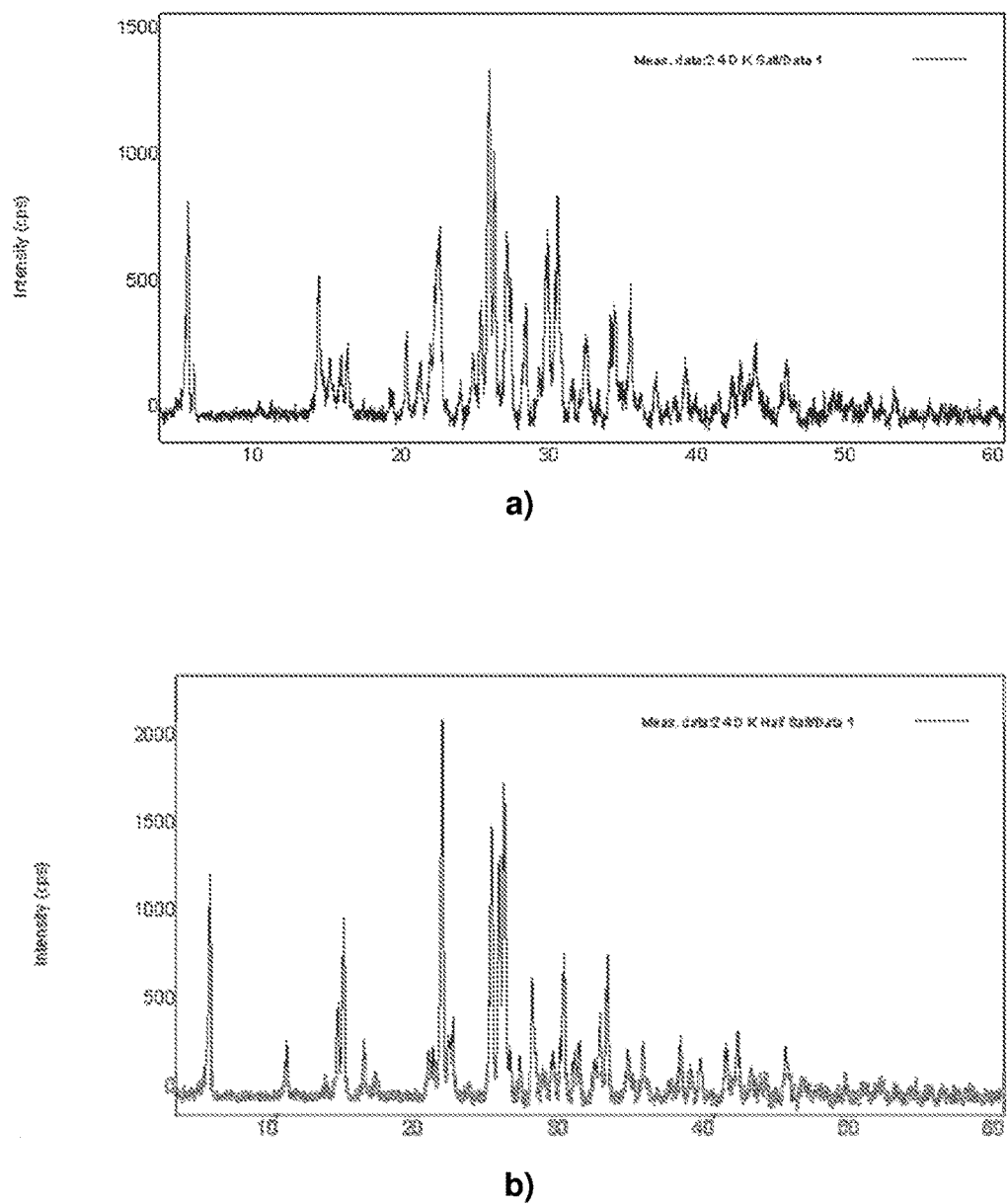
FIG. 1 shows the powder X-ray diffraction (PXRD) patterns of (a) the potassium full salt of 2,4-D and (b) the potassium half salt of 2,4-D.

Unless specifically limited otherwise, the term "alkyl", as well as derivative terms such as "arylalkyl", as used herein, include within their scope straight chain, branched chain and cyclic moieties. Unless specifically stated otherwise, each may be unsubstituted or substituted with one or more substituents selected from but not limited to halogen, hydroxy, alkoxy or alkylthio, provided that the substituents are sterically compatible and the rules of chemical bonding and strain energy are satisfied. The term "aryl" refers to a phenyl, indanyl or naphthyl group. The aryl group may be unsubstituted or substituted with one or more substituents selected from halogen, hydroxy, $C_1$-$C_6$ alkyl or $C_1$-$C_6$ alkoxy, provided that the substituents are sterically compatible and the rules of chemical bonding and strain energy are satisfied. The term "arylalkyl" refers to an alkyl group, such as $C_1$-$C_4$ alkyl groups, substituted with an aryl group.

The term "half salt" as used herein refers to a compound of the general formula (Ar—O—$(CHR)_n$COO)$_2$H$_1$M$_1$, wherein Ar, R and M are as defined herein, that is produced by the half neutralization of the carboxylic acid form of a synthetic auxin herbicide with a base (i.e., the molar ratio of the carboxylic acid to the cation M in the half salt is 2:1).

The term "full salt" as used herein refers to a compound of the general formula (Ar—O—$(CHR)_n$COO)M wherein Ar, R and M are as defined herein, that is produced by the full neutralization of the carboxylic acid form of a synthetic auxin herbicide with a base (i.e., the molar ratio of the carboxylic acid to the cation M in the full salt is 1:1).

Half salts of synthetic auxin herbicides and methods of their preparation and use are described herein. These half salts can be provided in admixture with agriculturally acceptable adjuvants and/or carriers, and in mixtures with other herbicides.

II. Half Salts

The half salt of the synthetic auxin herbicide has the following general formula I

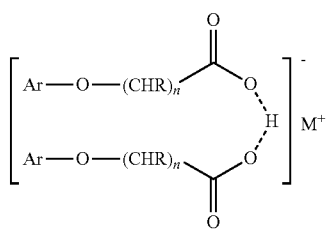

wherein R is independently H or $CH_3$, n is an integer 1, 2 or 3, and Ar is a phenyl or pyridine group substituted with one or more substituents selected from halogen, $C_1$-$C_6$ alkyl, $C_1$-$C_6$ haloalkyl, $C_1$-$C_6$ alkoxy, amino, $C_1$-$C_6$ alkylamino, and di($C_1$-$C_6$ alkyl)amino, and M is a cation selected from a metal cation or a tetrasubstitued ammonium cation.

Suitable metal cations include, but are not limited to, $Li^+$, $Na^+$, and $K^+$. Tetrasubstituted ammonium cations include, but are not limited to, N—(($C_1$-$C_{16}$) alkyl or arylalkyl) tri(($C_1$-$C_{16}$) alkyl)ammonium cations of the formula

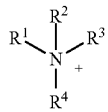

wherein $R^1$, $R^2$ and $R^3$ independently represents ($C_1$-$C_{16}$) alkyl or any two of $R^1$, $R^2$ and $R^3$ represent —$(CH_2)_n$— where n is an integer from 3-5 and $R^4$ represents (($C_1$-$C_{16}$) alkyl or arylalkyl). In some embodiments, N—(($C_1$-$C_{16}$) alkyl or arylalkyl) tri(($C_1$-$C_{16}$) alkyl)ammonium cations are those in which $R^1$, $R^2$, $R^3$ and $R^4$ are the same or where $R^1$, $R^2$ and $R^3$ are $CH_3$ and $R^4$ is ($C_2$-$C_{16}$) alkyl or arylalkyl. Suitable tetrasubstituted ammonium cations include, but are not limited to, tetramethyl ammonium, tetraethyl ammonium and choline (i.e., N,N,N-trimethylethanol ammonium).

Suitable synthetic auxin herbicides for use in the methods and compositions described herein include, but are not limited to, pyridinyloxyacetic acid herbicides such as fluroxypyr and triclopyr; phenoxyacetic herbicides such as 4-CPA, 2,4-D, 3,4-DA, and MCPA; phenoxybutyric acid herbicides such as 4-CPB, 2,4-DB, 3,4-DB, and MCPB; phenoxypropionic acid herbicides such as cloprop, 4-CPP, dichlorprop, 3,4-DP, fenoprop, mecoprop, and mecoprop-P. In some embodiments the synthetic auxin herbicides include 2,4-D, 2,4-DB, triclopyr, fluroxypyr, MCPA, MCPB, mecoprop, and mecoprop-P.

In some embodiments, the half salt is the sodium half salt of 2,4-D, the potassium half salt of 2,4-D, the lithium half salt of 2,4-D, or the choline half salt of 2,4-D.

In other embodiments, the half salt is the sodium half salt of triclopyr, the potassium half salt of triclopyr, the lithium half salt of triclopyr, or the choline half salt of triclopyr.

In other embodiments, the half salt is the sodium half salt of fluroxypyr, the potassium half salt of fluroxypyr, the lithium half salt of fluroxypyr, or the choline half salt of fluroxypyr.

A. Properties of the Half Salts

In some embodiments, the half salts have water solubilities within a pH range of from about 3 to about 6, from about 3 to about 5.5, from about 3.5 to about 6, from about 4 to about 6, or within a pH range of from about 4.5 to about 6.5, of less than about 10 wt %, less than about 5 wt %, less than about 4 wt %, less than about 3 wt %, less than about 2 wt %, less than about 1 wt %, less than about 0.5 wt %, or less than about 0.1 wt % with respect to the total weight of water and the half salt.

In some embodiments, the half salts have low solubility in organic solvents of low polarity such as, for example, one or more of petroleum distillates such as aromatic hydrocarbons derived from benzene, such as toluene, xylenes, other alkylated benzenes and the like, and naphthalene derivatives, aliphatic hydrocarbons such as hexane, octane, cyclohexane, and the like, mineral oils from the aliphatic or isoparaffinic series, and mixtures of aromatic and aliphatic hydrocarbons; halogenated aromatic or aliphatic hydrocarbons; vegetable, seed or animal oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like, and $C_1$-$C_6$ mono-esters derived from vegetable, seed or animal oils; $C_1$-$C_6$ dialkyl amides of $C_6$-$C_{20}$ saturated and unsaturated aliphatic carboxylic acids; $C_1$-$C_{12}$ esters of aromatic carboxylic acids and dicarboxylic acids and $C_1$-$C_{12}$ esters of aliphatic and cyclo-aliphatic carboxylic acids. In some embodiments low solubility, as used herein, refers to a solubility of less than about 5 wt %, less than about 4 wt %, less than about 3 wt %, less than about 2 wt %, less than about 1 wt %, less than about 0.5 wt %, or less than about 0.1 wt % with respect to the total weight of the solvent and the half salt.

In some embodiments, the half salts have moderate to good solubility in protic solvents such as, for example, alcohols like methanol, polyalcohols like ethylene glycol, propylene glycol and derivatives thereof, glycerol, and mixtures of one or more protic solvents with water. In some embodiments moderate to good solubility, as used herein, refers to a solubility of the half salt of not less than about 1 wt %, not less than about 2 wt %, not less than about 3 wt %, not less than about 4 wt %, not less than about 5 wt %, not less than about 7 wt %, not less than about 9 wt %, not less than about 10 wt %, not less than about 15 wt %, or not less than about 20 wt % with respect to the total weight of the solvent and the half salt.

In some embodiments, the half salts have lower volatility than the corresponding carboxylic acid, amine salt or ester form of the synthetic auxin herbicides.

B. Analytical Characterization of the Half Salts

The half salts of the synthetic auxin herbicides may be characterized analytically, for example, by one or more of the following methods: (1) powder X-ray diffraction (PXRD) whereby the major peaks of the X-ray diffraction pattern are expressed in terms of 2-theta (2θ) angles, (2) differential scanning calorimetry (DSC), (3) ion chromatography, (4) reverse phase HPLC, (5) elemental analysis, and (6) spectral methods such as NMR, IR and Raman.

III. Herbicidal Compositions

The low solubility of the half salts in water and organic solvents of low polarity make these solvents suitable for preparing suspension concentrate compositions wherein the half salts are suspended as small particles (i.e., about 0.5-50 microns in average size) in water (SC composition) or in an organic solvent of low polarity (OD composition).

A. Aqueous Suspension Concentrates (SC)

In some embodiments, the described herbicidal compositions include aqueous suspension concentrates (SC) which include, with respect to the total composition, from about 1 to about 50 weight percent (wt %), on an acid equivalent (AE) basis, of the half-salt of the synthetic auxin herbicide and, optionally, one or more additional inert ingredients. Upon dilution in water, the described aqueous suspension concentrates form stable, homogeneous spray mixtures that may be readily used in spray applications to control plant growth.

In some embodiments, the aqueous suspension concentrate includes the sodium half salt of 2,4-D, the potassium half salt of 2,4-D, the lithium half salt of 2,4-D, or the choline half salt of 2,4-D.

In some embodiments, the aqueous suspension concentrate includes the sodium half salt of triclopyr, the potassium half salt of triclopyr, the lithium half salt of triclopyr, or the choline half salt of triclopyr.

In some embodiments, the aqueous suspension concentrate includes the sodium half salt of fluroxypyr, the potassium half salt of fluroxypyr, the lithium half salt of fluroxypyr, or the choline half salt of fluroxypyr.

B. Aqueous Premix Suspension Concentrates

Additionally described herein are aqueous premix suspension concentrates that include, with respect to the total composition, from about 1 to about 50 weight percent (wt %), on an acid equivalent (AE) basis, of the half salt of the synthetic auxin herbicide and from about 1 to about 50 wt % of a second herbicide selected from glyphosate and glufosinate, or an agronomically acceptable salt thereof. Suitable salts of glyphosate and glufosinate for use in the aqueous premix suspension concentrates include, but are not limited to, glyphosate dimethyl ammonium, glyphosate potassium, glyphosate isopropyl ammonium, and glufosinate ammonium. Upon dilution in water, the described aqueous premix suspension concentrates form stable, homogeneous mixtures that are readily used in spray applications to control plant growth.

The described aqueous premix suspension concentrates may include, on an acid equivalent (AE) basis, a weight ratio of the half salt of the synthetic auxin herbicide to the glyphosate salt of from about 1:5 to 5:1, 1:4 to 4:1, 1:3 to 3:1, 1:2 to 2:1, 1:1.5 to 1.5:1, 1:2.3 to 2.3:1, 1:2.5 to 2.5:1, 1:3.5 to 3.5:1, or from about 1:4.5 to 4.5:1.

The described aqueous premix suspension concentrates may include, on an acid equivalent (AE) basis, a weight ratio of the half salt of the synthetic auxin herbicide to the glufosinate salt of from about 1:5 to 5:1, 1:4 to 4:1, 1:3 to 3:1, 1:2 to 2:1, or from about 1:1.5 to 1.5:1.

In some embodiments, the aqueous premix suspension concentrate includes a half salt of a synthetic auxin herbicide and a water soluble salt of glyphosate.

In other embodiments, the aqueous premix suspension concentrate includes the sodium half salt of 2,4-D and the dimethyl ammonium salt of glyphosate, the sodium half salt of 2,4-D and the potassium salt of glyphosate, or the sodium half salt of 2,4-D and the isopropyl ammonium salt of glyphosate.

In other embodiments, the aqueous premix suspension concentrate includes the potassium half salt of 2,4-D and the dimethyl ammonium salt of glyphosate, the potassium half salt of 2,4-D and the potassium salt of glyphosate, or the potassium half salt of 2,4-D and the isopropyl ammonium salt of glyphosate.

In other embodiments, the aqueous premix suspension concentrate includes the choline half salt of 2,4-D and the dimethyl ammonium salt of glyphosate, the choline half salt of 2,4-D and the potassium salt of glyphosate, or the choline half salt of 2,4-D and the isopropyl ammonium salt of glyphosate.

In some embodiments, the aqueous premix suspension concentrate includes a half salt of a synthetic auxin herbicide and a water soluble salt of glufosinate.

In some embodiments, the aqueous premix suspension concentrate includes the sodium half salt of 2,4-D and the ammonium salt of glufosinate, the potassium half salt of 2,4-D and the ammonium salt of glufosinate, or the choline half salt of 2,4-D and the ammonium salt of glufosinate.

C. Dry Concentrates

Additionally described herein are dry concentrates that include, with respect to the total composition, from about 1 to about 90 weight percent (wt %), on an acid equivalent (AE) basis, of a half salt of the synthetic auxin herbicides and, optionally, one or more additional inert ingredients. The dry concentrates may be a powder, a granule, or a dispersible granule. Upon dilution in water, the described dry concentrates form stable, homogeneous spray mixtures that may be readily used in spray applications to control plant growth.

In some embodiments, the dry concentrate includes the sodium half salt of 2,4-D, the potassium half salt of 2,4-D, the lithium half salt of 2,4-D or the choline half salt of 2,4-D.

In other embodiments, the dry concentrate includes the sodium half salt of triclopyr, the potassium half salt of triclopyr, the lithium half salt of triclopyr, or the choline half salt of triclopyr.

In other embodiments, the dry concentrate includes the sodium half salt of fluroxypyr, the potassium half salt of fluroxypyr, the lithium half salt of fluroxypyr, or the choline half salt of fluroxypyr.

D. Dry Premix Concentrates

Additionally described herein are dry premix concentrates that include, with respect to the total composition, from about 1 to about 75 weight percent (wt %), on an acid equivalent (AE) basis, of the half salt of a synthetic auxin herbicide and from about 1 to about 75 wt % of a second herbicide selected from glyphosate and glufosinate, or an agronomically acceptable salt thereof. Suitable salts of glyphosate and glufosinate for use in the dry premix concentrates include, but are not limited to, glyphosate dimethyl ammonium, glyphosate potassium, glyphosate isopropyl ammonium, and glufosinate ammonium. The dry premix concentrate may be a powder, a granule, or a dispersible granule. Upon dilution in water, the dry premix concentrate forms a stable, homogeneous mixture that is readily used in spray applications to control plant growth.

In some embodiments, the dry premix concentrate includes a half salt of a synthetic auxin herbicide and a water soluble salt of glyphosate.

In other embodiments, the dry premix concentrate includes the sodium half salt of 2,4-D and the dimethyl ammonium salt of glyphosate, the sodium half salt of 2,4-D and the potassium salt of glyphosate, or the sodium half salt of 2,4-D and the isopropyl ammonium salt of glyphosate.

In other embodiments, the dry premix concentrate includes the potassium half salt of 2,4-D and the dimethyl ammonium salt of glyphosate, the potassium half salt of 2,4-D and the potassium salt of glyphosate, or the potassium half salt of 2,4-D and the isopropyl ammonium salt of glyphosate.

In other embodiments, the dry premix concentrate includes the choline half salt of 2,4-D and the dimethyl ammonium salt of glyphosate, the choline half salt of 2,4-D and the potassium salt of glyphosate, or the choline half salt of 2,4-D and the isopropyl ammonium salt of glyphosate.

In some embodiments, the dry premix concentrate includes a half salt of a synthetic auxin herbicide and a water soluble salt of glufosinate.

In some embodiments, the dry premix concentrate includes the sodium half salt of 2,4-D and the ammonium salt of glufosinate, the potassium half salt of 2,4-D and the ammonium salt of glufosinate, or the choline half salt of 2,4-D and the ammonium salt of glufosinate.

E. Aqueous Herbicide Spray Mixtures

Another embodiment concerns an aqueous herbicide spray mixture containing a half-salt of a synthetic auxin herbicide and, optionally, a second herbicide and various inert ingredients. The aqueous herbicide spray mixture may be prepared by diluting in water one or more of an aqueous or dry herbicide concentrate or by tank mixing the components of the spray solution. Such a spray mixture may comprise, with respect to the total spray solution, from about 0.1 to about 10 weight percent, or from about 0.1 to about 5 weight percent of the half-salt of a synthetic auxin herbicide, optionally, a water soluble salt of glyphosate or glufosinate, and optionally, additional inert ingredients.

IV. Method of Preparation

The half salts of the synthetic auxin herbicides described herein are prepared by combining the carboxylic acid form of the synthetic auxin herbicide, wherein Ar, R and n are as previously defined, with one half molar equivalent of a base. Suitable solvents useful for

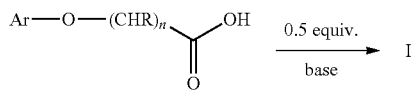

preparing the half salts of the synthetic auxin herbicides described herein may include, but are not limited to, water, alcohols such as methanol, ethanol, ethylene glycol, and propylene glycol, derivatives of ethylene and propylene glycol such as alkylated ethylene glycols and the like; ethers such as tetrahydrofuran and dioxane; nitriles such as acetonitrile and butyronitrile; N,N-dialkyl amides such as, N-methyl-2-pyrrolidinone and N,N-dimethyl alkylamides; and mixtures thereof. The half salts prepared as described herein may be isolated using standard methods.

Bases useful for preparing the half salts of the synthetic auxin herbicides described herein include the alkali metal hydroxides such as, for example, sodium hydroxide, potassium hydroxide, and lithium hydroxide, and the tetrasubstituted ammonium hydroxides such as, for example, tetramethylammonium hydroxide, tetraethylammonium hydroxide and choline hydroxide.

V. Method of Use

The term "herbicide" is used herein to mean an active ingredient that kills, controls, or otherwise adversely modifies the growth of plants. A herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, and established vegetation.

A. Controlling Plant Growth

Herbicidal activity is exhibited by the compositions described herein when the compositions are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action.

Application rates of about 1 to about 2,000 grams per hectare (g/Ha) are generally employed in both postemergence and preemergence applications. The higher rates designated generally give non-selective control of a broad variety of undesirable vegetation. The lower rates typically give selective control and can be employed in the locus of crops.

Also described herein is a method of controlling undesirable vegetation by contacting the vegetation or the locus thereof with or applying to the soil to prevent emergence of the vegetation a herbicidally effective amount of the half salt compositions described herein. The described compositions offer comparable herbicidal efficacy, on an acid equivalent (AE) basis, when compared to existing alkylamine salt compositions of the synthetic auxin herbicides such as, for example, 2,4-D dimethylamine.

The compositions described herein can additionally be employed to control undesirable vegetation in many crops that have been made tolerant to or resistant to them or to other herbicides by genetic manipulation or by mutation and selection. The compositions described herein can, further, be used in conjunction with glyphosate, glufosinate, dicamba, or imidazolinones on glyphosate-tolerant, glufosinate-tolerant, dicamba-tolerant, imidazolinone-tolerant, or 2,4-D-tolerant crops. The compositions described herein are preferably used in combination with herbicides that are selective for the crop being treated and complement the spectrum of weeds controlled by these compounds at the application rate employed. The compositions described herein are preferably applied at the same time as other complementary herbicides, either as a combination formulation or as a tank mix. Similarly the compositions described herein can be used in conjunction with acetolactate synthase inhibitors on acetolactate synthase inhibitor tolerant crops.

B. Reducing Volatility

Further described herein is a method of reducing the volatility of a synthetic auxin herbicide in spray applications for the control of unwanted plant growth by using the half salt of the synthetic auxin herbicide as described herein. Especially useful synthetic auxin herbicides that will exhibit reduced volatility when used in their corresponding half salt chemical forms are 2,4-D, 2,4-DB, triclopyr, fluroxypyr, MCPA, MCPB, mecoprop, and mecoprop-P.

C. Reducing Soil Mobility

Further described herein is a method of reducing the soil mobility of a synthetic auxin herbicide by using the half salt of the synthetic auxin herbicide as described herein. Especially useful synthetic auxin herbicides that will exhibit reduced soil mobility when used in their corresponding half salt chemical forms include 2,4-D, 2,4-DB, triclopyr, fluroxypyr, MCPA, MCPB, mecoprop, and mecoprop-P.

VI. Use with Other Agricultural Active Ingredients

The compositions described herein can also be used in combination with other agricultural active ingredients such as, for example, herbicides, insecticides, fungicides, plant growth regulators, safeners, various mixtures and combinations of these, and the like. These mixtures and combinations may be pre-mix concentrates or spray solutions prepared by either diluting such a concentrate or tank-mixing the components of the spray solution, or they may be applied sequentially with the other agricultural active ingredient or ingredients.

A. Herbicides

Herbicides that may be employed in conjunction with the compositions described herein include, but are not limited to, 2,4-DEB, 2,4-DEP, 2,3,6-TBA, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clomazone, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyperquat, cyprazine, cyprazole, cypromid, daimuron, dalapon, dazomet, delachlor, desmedipham, desmetryn, di-allate, dicamba, dichlobenil, dichloralurea, dichlormate, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoxasulfone, fenteracol, fentrazamide, fenuron, ferrous sulfate, flamprop, flamprop-M, flazasulfuron, florasulam, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, flurtamone, fluthiacet, fomesafen, foramsulfuron, fosamine, furyloxyfen, halosafen, halosulfuron, haloxydine, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, karbutilate, ketospiradox, lactofen, lenacil, linuron, MAA, MAMA, medinoterb, mefenacet, mefluidide, mesoprazine, mesosulfuron, mesotrione, metam, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, pretilachlor, primisulfuron, procyazine, prodiamine, profluazol, profluralin, profoxydim, proglinazine, prometon, prometryn, propachlor, propanil, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, rhodethanil, rimsulfuron, saflufenacil, S-metolachlor, sebuthylazine, secbumeton, sethoxydim, siduron, simazine, simeton, simetryn, SMA, sulcotrione, sulfallate, sulfentrazone, sulfometuron, sulfosulfuron, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, triallate, triasulfuron, triaziflam, tribenuron, tricamba, tridiphane, trietazine, trifloxysulfuron, trifluralin, triflusulfuron, trifopsime, trihydroxytriazine, trimeturon, tripropindan, tritac, tritosulfuron, vernolate, xylachlor, and salt or ester derivatives thereof.

Additional examples of herbicide of active ingredients useful in the solid herbicidal compositions described herein and described in Group A (and their salts and esters) include, for example, compounds disclosed in U.S. Pat. Nos. 7,314, 849 B2; 7,300,907 B2; 7,786,044 B2; and 7,642,220 B2.

In some embodiments, the herbicide is a compound having the following formula

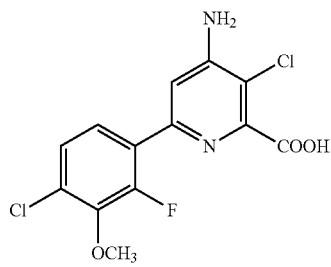 [SMILES: COc1c(Cl)ccc(-c2cc(N)c(Cl)c(C(=O)O)n2)c1F]

or a $C_1$-$C_6$ alkyl ester or salt thereof, e.g., the methyl ester, also known as halauxifen-methyl.

In some embodiments, the herbicide is a compound having the following formula

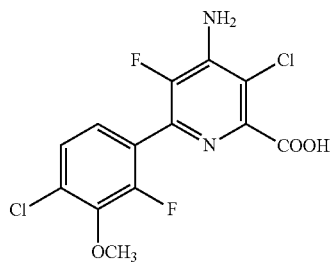 [SMILES: COc1c(Cl)ccc(-c2nc(C(=O)O)c(Cl)c(N)c2F)c1F]

or a $C_1$-$C_{12}$ alkyl or $C_7$-$C_{12}$ arylalkyl ester or salt thereof, e.g., the benzyl ester, referred to herein as Compound A.

In some embodiments, herbicides that may be employed in conjunction with the compositions described herein include one or more of acetochlor, aminocyclopyrachlor, aminopyralid, atrazine, benfluralin, clopyralid, cloransulam, dicamba, ethalfluralin, florasulam, flumetsulam, isoxaben, metosulam, penoxsulam, picloram, propanil, propyzamide, pyroxsulam, tebuthiuron, thiazopyr, trifluralin, and salts or esters thereof.

B. Safeners

The compositions described herein can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148, and N-phenylsulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to the compositions described herein in sensitive plants can be treated. Some crops (e.g. cotton) have been made tolerant to auxinic herbicides such as 2,4-dichlorophenoxyacetic acid. The compositions described herein derived from auxin herbicides may be used to treat such resistant crops or other auxin herbicide tolerant crops.

VIII. Adjuvants, Carriers and Surface-Active Agents

While it is possible to utilize the compositions described herein directly as herbicides, it is preferable to use them in mixtures containing a herbicidally effective amount of the compositions described herein along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compositions described herein or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions, or suspensions.

Suitable agricultural adjuvants and carriers that are useful in preparing the compositions of the half salts described herein are well known to those skilled in the art.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil, and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids, and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

Surface-active agents (i.e., surfactants) can be incorporated into the compositions described herein. Such surface-active agents are advantageously employed in both solid and liquid compositions, especially those designed to be diluted with carrier before application. The surface-active agents can be anionic, cationic, or nonionic in character and can be employed as emulsifying agents, wetting agents, suspending agents, or for other purposes. Surfactants conventionally used in the art of formulation and which may also be used in the compositions described herein are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate and sodium lauryl ether sulfates; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; ethoxylated amines, such as tallowamine ethoxylate; betaine surfactants, such as cocoamidopropyl betaine; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Adjuvants that can be used to reduce spray drift can be added to the half salt compositions or used in spray solutions containing the half salts include, but are not limited to, microencapsulated oils, self emulsifying esters, ethoxylated natural oils, amine and amine oxide surfactants, alkylbenzene sulfonate surfactants, latex-stabilized emulsions, naturally derived oils such as fatty acid alkyl esters, fatty acid amides, and triglyceride fatty acid esters, aromatic esters, paraffinic oils, petroleum derived oils, and mixtures thereof.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions of polymeric complexes of herbicidal carboxylic acids described herein may also contain other compatible components, for example, other herbicides, plant growth regulants, fungicides, insecticides, and the like and can be formulated with liquid fertilizers or solid, particulate fertilizer carriers such as ammonium nitrate, urea and the like.

The compositions described herein are typically diluted with an inert carrier, such as water, before application. The diluted compositions applied to weeds or the locus of weeds generally contain about 0.0001 to about 1 weight percent of the active ingredient and preferably contain about 0.001 to about 0.05 weight percent.

The compositions described herein can be applied to weeds or their locus by the use of conventional ground or aerial dusters, sprayers, and granule applicators, by addition to irrigation water, and by other conventional means known to those skilled in the art.

The following Examples are presented to illustrate various aspects of the compositions described herein and should not be construed as limitations to the claims.

Example 1

Preparation of Synthetic Auxin Half Salts

Method A—Preparation of Auxin Half Salts Using an Organic Solvent
Sample 1: 2,4-D Potassium Half Salt
To a solution of 69.29 g of methanol and 24.25 g (0.106 mole) of 2,4-dichlorophenoxyacetic acid (97% assay) was added 5.97 g (0.053 mole) of 50% aqueous potassium hydroxide solution. A suspension was formed and was then concentrated on a rotavap at 50° C. to provide a dry powder of the half salt. Analysis of the half salt by HPLC and ion chromatography showed the isolated half salt had a 2:1 molar ratio of 2,4-D acid to potassium. The melting point of the 2,4-D potassium half salt was determined by DSC analysis to be 226° C.

Sample 2: 2,4-D Sodium Half Salt
The 2,4-D sodium half salt was prepared in a similar manner to that of the 2,4-D potassium half salt using sodium hydroxide and following Method A. HPLC and ion chromatography analyses showed the isolated half salt had a 2:1 molar ratio of 2,4-D acid to sodium. The melting point of the 2,4-D sodium half salt was determined by DSC analysis to be 186° C.

Sample 3: 2,4-D Lithium Half Salt
The 2,4-D lithium half salt was prepared in a similar manner to that of the 2,4-D potassium half salt using lithium hydroxide and following Method A. HPLC and ion chromatography analyses showed the isolated half salt had a 2:1 molar ratio of 2,4-D acid to lithium.

Sample 4: 2,4-D Choline Half Salt
The 2,4-D choline half salt was prepared in a similar manner to that of the 2,4-D potassium half salt using choline hydroxide and following Method A. HPLC and ion chromatography analyses showed the isolated half salt had a 2:1 molar ratio of 2,4-D acid to choline. The melting point of the 2,4-D choline half salt was determined by DSC analysis to be 240° C.

Sample 5: Triclopyr Choline Half Salt
The triclopyr choline half salt was prepared in a similar manner to that of the 2,4-D potassium half salt using triclopyr and choline hydroxide and following Method A. HPLC and ion chromatography analyses showed the isolated half salt had a 2:1 molar ratio of triclopyr to choline. The melting point of the triclopyr choline half salt was determined by DSC analysis to be 257° C.

Method B—Preparation of Auxin Half Salts Using Water Solvent
Sample 6: 2,4-D Potassium Half Salt
A 35 weight percent suspension of 2,4-dichlorophenoxy acetic acid (97% assay) was formed in water with the aid of a Silverson homogenizer. The suspension was then wet milled using an Eiger mill for one pass using 1.0-1.3 mm glass beads at 80% chamber volume. The resulting milled suspension was treated with one half of a molar equivalent of 50% aqueous potassium hydroxide solution and then wet milled for two additional passes through the Eiger mill. In order to remove the water, the milled suspension was poured onto heated rotating drums (drum dryer), producing a white crystalline powder that was air milled to reduce the particle size.

Example 2

Powder X-Ray Diffraction (PXRD) Analysis of the Synthetic Auxin Half Salts

The PXRD analyses were conducted on a Rigaku MiniFlex II Desktop X-Ray Diffractometer using 30 kV (15 mA) X-rays, a scan speed of 5 degrees/minute, and a scan range of 3-60 degrees (2-theta; 2θ). The powder X-ray diffraction pattern of the auxinic half salts shown in FIGS. 1b), 2b) and 3b) are substantially different from the powder X-ray diffraction patterns of the corresponding auxinic full salts shown in FIGS. 1a), 2a) and 3a).

FIG. 1 shows the powder X-ray diffraction (PXRD) pattern of (a) the potassium full salt of 2,4-D and (b) the potassium half salt of 2,4-D. Table 1 lists the 2θ values of the major peaks shown in the PXRD patterns for the two salts shown in FIG. 1.

TABLE 1

| 2,4-D Potassium Half Salt 2θ | 2,4-D Potassium Full Salt 2θ |
| --- | --- |
| 5.3 | 4.9 |
| 14.1 | 13.7 |
| 14.5 | 21.9 |
| 21.3 | 24.7 |
| 24.7 | 25.2 |
| 25.3 | 25.6 |
| 25.6 | 26.4 |
| 27.5 | 29.2 |
| 29.7 | 29.9 |
| 32.7 | 34.8 |

Figure 2:
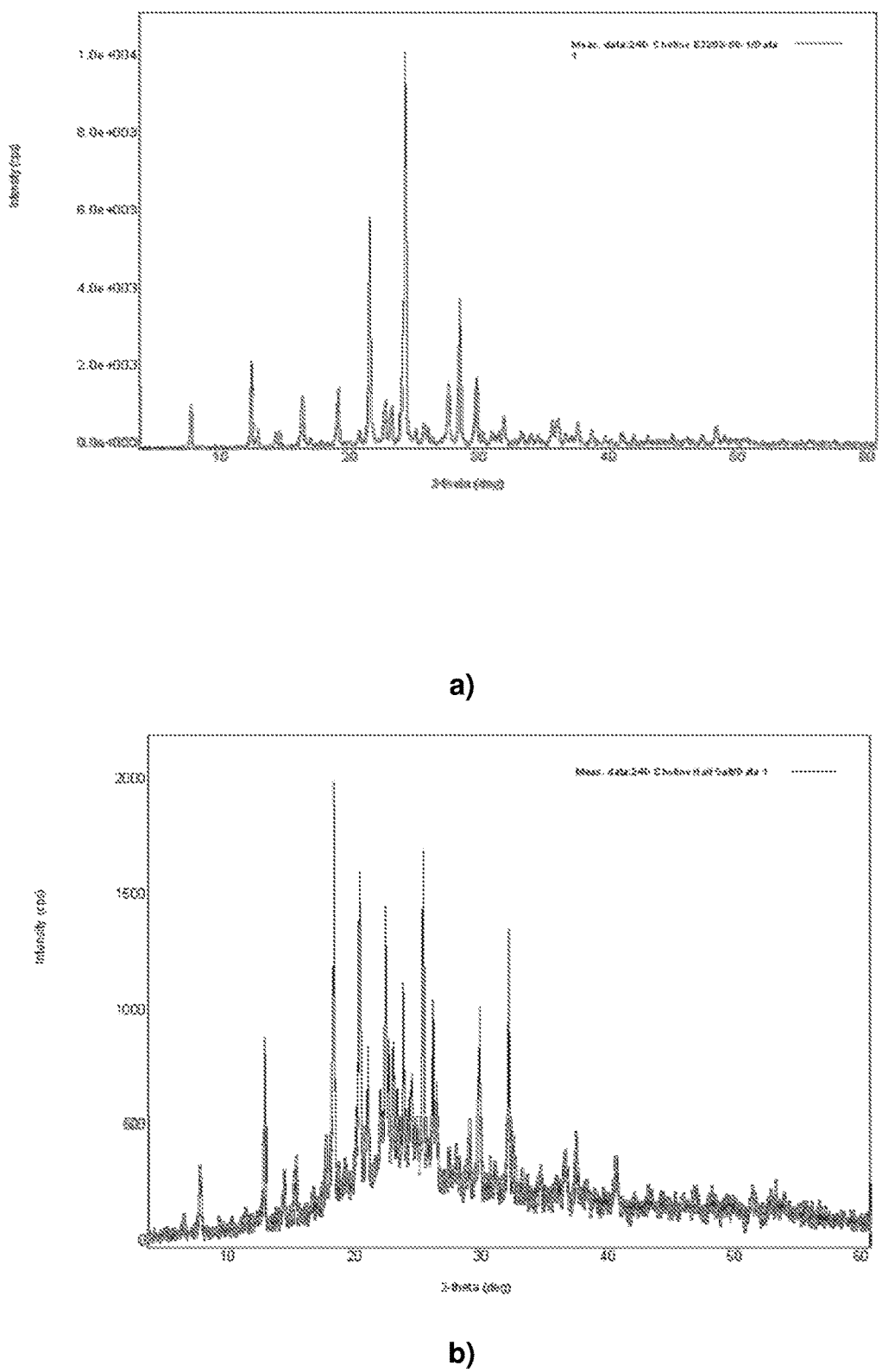
FIG. 2 shows the powder X-ray diffraction (PXRD) patterns of (a) the choline full salt of 2,4-D and (b) the choline half salt of 2,4-D.

FIG. 2 shows the powder X-ray diffraction (PXRD) pattern of (a) the choline full salt of 2,4-D and (b) the choline half salt of 2,4-D. Table 2 lists the 2θ values of the major peaks shown in the PXRD patterns for the two salts shown in FIG. 2.

TABLE 2

| 2,4-D Choline Half Salt 2θ | 2,4-D Choline Full Salt 2θ |
| --- | --- |
| 12.27 | 7.02 |
| 17.709 | 11.69 |
| 19.717 | 15.62 |
| 21.771 | 18.377 |
| 21.977 | 20.745 |
| 22.391 | 20.818 |
| 23.183 | 21.983 |
| 24.757 | 22.466 |
| 29.196 | 23.5 |
| 31.49 | 23.594 |
|  | 26.939 |
|  | 27.818 |
|  | 29.136 |

Figure 3:
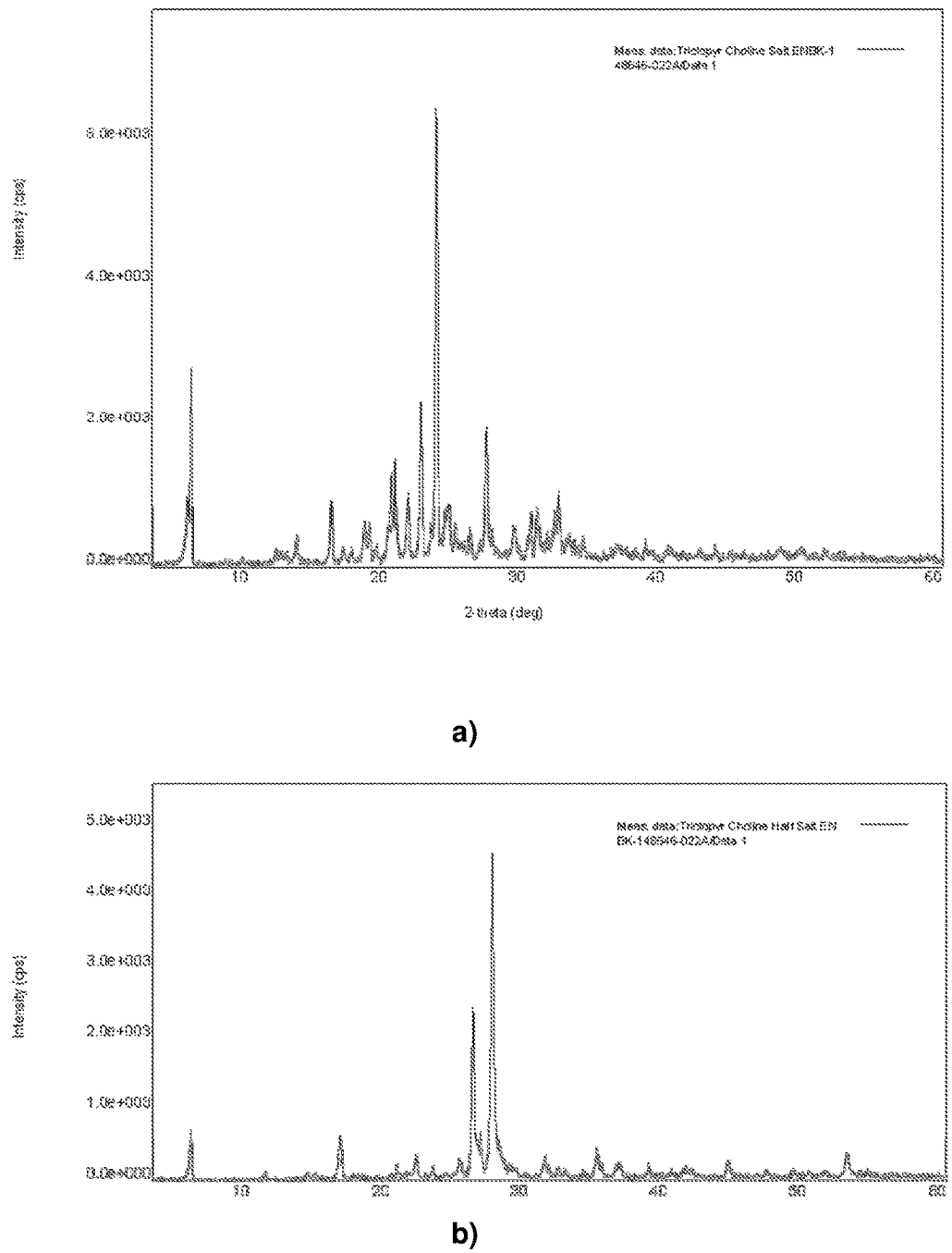
FIG. 3 shows the powder X-ray diffraction (PXRD) patterns of (a) the choline full salt of triclopyr and (b) the choline half salt of triclopyr.

FIG. 3 shows the powder X-ray diffraction (PXRD) pattern of (a) the choline full salt of triclopyr and (b) the choline half salt of triclopyr. Table 3 lists the 2θ values of the major peaks shown in the PXRD patterns for the two salts shown in FIG. 3.

TABLE 3

| Triclopyr Choline Half Salt 2θ | Triclopyr Choline Salt 2θ |
| --- | --- |
| 5.7 | 5.8 |
| 16.5 | 15.9 |
| 26.0 | 20.3 |
| 27.4 | 20.5 |
|  | 21.4 |
|  | 22.4 |
|  | 23.5 |
|  | 27.1 |
|  | 32.3 |

Example 3

Preparation of Liquid Herbicidal Compositions Containing the Synthetic Auxin Half Salts Described Herein Sample 7: Glufosinate-Ammonium Aqueous Composition A 12.25 g quantity of glufosinate-ammonium (GluA) technical (95.2% purity, 11.66 g ai), 62.49 g of DI water and 25.26 g Steol CS-460 (sodium lauryl ether sulfate surfactant (LES), Stepan) were combined to yield 100 g of clear, liquid concentrate containing 11.66 wt % ai, (10.66 wt % ae) of glufosinate-ammonium.

Sample 8: 2,4-D Potassium Half-Salt Aqueous Suspension Concentrate

To each of two 20-ml plastic vials was added 2.21 g of 2,4-D potassium half-salt technical (90.4 wt %, 2.0 g ai) and 2.79 g of an SC blank solution consisting of 0.0837 g of Pluronic P-105, 0.0558 g of Morwet D-425, 0.0279 g of Antifoam B and 2.62 g of DI water. A 30 g quantity of ⅛ in. steel balls was then added to each vial and the samples were milled for 15 min in a Retsch shaker at 100% shaking intensity. The resulting milled concentrates were separated from the steel balls and combined using a disposable plastic pipette. The resulting suspension concentrate contained 40 wt % ai (36.8 wt % ae) of 2,4-D potassium half-salt.

Sample 9: Glufosinate-Ammonium/2,4-D Potassium Half-Salt Aqueous SC Premix

A 2,4-D potassium half salt/glufosinate-ammonium suspension concentrate premix with a 2.06:1 (wt % ae/wt % ae) 2,4-D potassium half salt to glufosinate-ammonium ratio was prepared by combining 2.0 g of the 2,4-D potassium half-salt suspension concentrate (Sample 6) with 3.35 g of the glufosinate-ammonium aqueous concentrate (Sample 5) to yield a premix concentrate containing 13.77 wt % ae of 2,4-D potassium half salt and 6.67 wt % ae of glufosinate-ammonium.

Example 4

Preparation of Dry (Solid) Herbicidal Compositions Containing the Synthetic Auxin Half Salts Described Herein Sample 10: 2,4-D Potassium Half-Salt Dispersible Granule (DG)

The ingredients shown in Table 4 were combined and blended to provide a blended powder with a d(0.5) of about 3-5 microns (μm) and a d(0.9) of <10 μm. The powder was mixed with water to form a wetted powder containing about 27-29 wt % water that was then extruded through a basket extruder (1.0 mm screen size) to provide granules. The granules were dried at 45° C. to a final moisture level of 1-2 wt % and then were sieved (No. 12 and No. 40 sieves) to remove fines and oversized particles. The sieved granules were added to 342 ppm hardness water and fully dispersed in 50 seconds using 4 inversions in a 250 mL graduated glass cylinder. The dispersed mixture was passed through a 45 micron sieve and no material was collected on the sieve.

TABLE 4

Composition of Dry Herbicidal Composition Containing 2,4-D Potassium Half Salt (Sample 10)

| Ingredients | Amount (g/kg) |
| --- | --- |
| 2,4-D K Half Salt (Sample 6) | 500 |
| Polyfon O | 70 |

TABLE 4-continued

Composition of Dry Herbicidal Composition Containing
2,4-D Potassium Half Salt (Sample 10)

| Ingredients | Amount (g/kg) |
|---|---|
| Stepanol ME Dry | 30 |
| Pergopak M | 125 |
| Kaolin Clay (ASP 602) | 275 |
| Total | 1000 |

Sample 11: 2,4-D Potassium Half-Salt Dispersible Granule (DG)

In a similar manner to that described for the preparation of Sample 10, the ingredients in Table 5 were converted into dispersible granules that were dried and sieved as before. The sieved granules were added to 342 ppm hardness water and were fully dispersed in 75 seconds using 7 inversions in a 250 mL graduated glass cylinder. The dispersed mixture was passed through a 45 micron sieve and no material was collected on the sieve.

TABLE 5

Composition of Dry Herbicidal Composition Containing
2,4-D Potassium Half Salt (Sample 11)

| Ingredients | Amount (g/kg) |
|---|---|
| 2,4-D K Half Salt | 500 |
| Morwet D-425 | 75 |
| Stepanol ME Dry | 30 |
| Pergopak M | 125 |
| Citric acid | 30 |
| Kaolin Clay (ASP 602) | 240 |
| Total | 1000 |

Sample 12: Glufosinate-Ammonium/2,4-D Potassium Half-Salt Dispersible Granule (DG)

Using the ingredients and amounts shown in Table 6, Steol CS-460 adjuvant (Stepan) was infused into ZeoFree 5180 silica (Huber) and then the infused sample was heated at 45° C. to remove excess moisture. The dried, infused silica sample and the remaining ingredients were then combined, mixed well, wetted with water (27-29 wt %) and extruded with a basket extruder (1.0 mm screen size). The resulting granules were dried at 45° C. and then sieved (No. 12 and No. 40 sieves) to remove fines and oversized particles. The sieved granules were added to 342 ppm hardness water and were fully dispersed in 165 seconds using 17 inversions in a 250 mL graduated glass cylinder. The dispersed mixture was passed through a 45 micron sieve and no material was collected on the sieve.

TABLE 6

Composition of Dry Herbicidal Composition Containing Glufosinate-ammonium and 2,4-D Potassium Half Salt (Sample 12)

| Ingredients | Amount (g/kg) |
|---|---|
| 2,4-D K Half Salt | 250.0 |
| Glufosinate-ammonium | 121.4 |
| Steol CS-460 | 262.1 |
| Polyox N-10 (WSP) | 0.5 |
| Geropon T-77 | 30.0 |
| Corn starch | 40.0 |
| Metasperse 550S | 10.0 |
| Cellulose (BH-100) | 35.0 |
| ZeoFree 5180 | 251.0 |
| Total | 1000.0 |

Example 5

Volatility Determination of 2,4-D Potassium Half Salt and 2,4-D Acid, Ester and Ammomium Salt Standards The volatility of the 2,4-D potassium half salt (as a concentrated aqueous suspension) was compared to that of 2,4-D acid (as technical solid), 2,4-D ethylhexyl ester (EHE, as technical liquid), and 2,4-D dimethylammonium (DMA) and 2,4-D dimethylethanolammonium (DMEA) salts (both as concentrated aqueous solutions) by thermogravimetric analysis (TGA) weight loss at elevated temperature. Each of the 2,4-D samples was added in turn (approximately 25-30 mg) to the reservoir cup of a TA Instruments Model 2050 TGA instrument. The temperature was maintained at 120° C. and the weight loss was recorded as a function of time.

Figure 4:
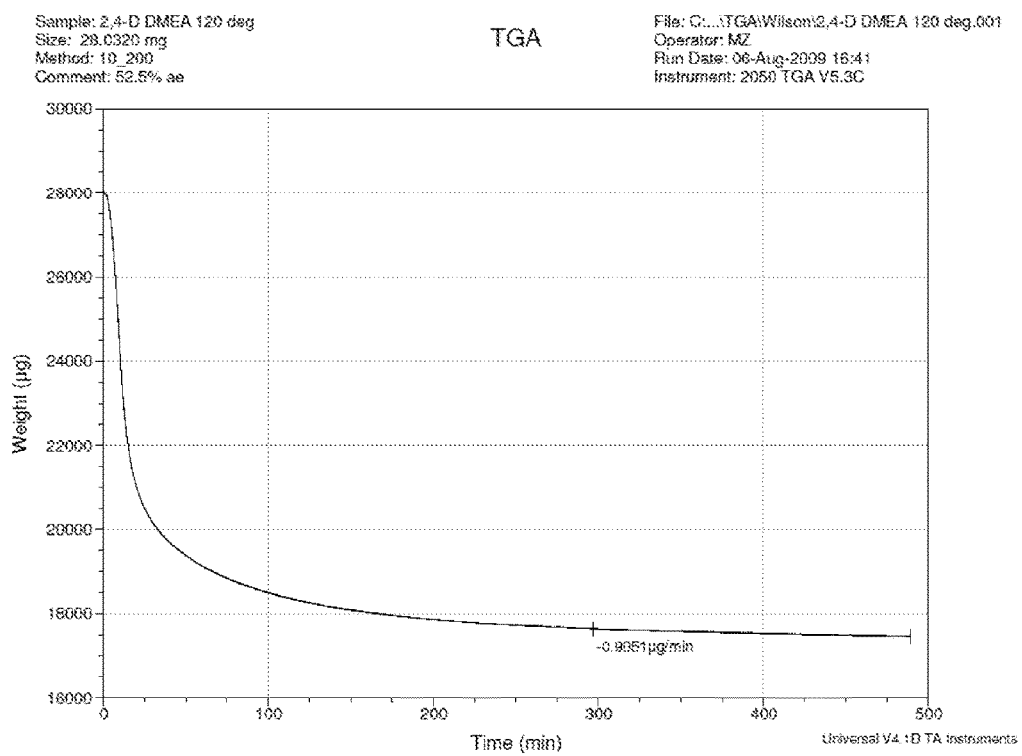
FIG. 4 shows the results of a thermogravometric analysis (TGA) weight loss determination at elevated temperature for the DMEA salt solution of 2,4-D.

For the water-containing samples, rapid weight loss was observed during water removal followed by a linear region (constant rate of loss). Linear curve fitting was applied in this region of the curve to determine rate of 2,4-D loss in μg/min. FIG. 4 shows a typical weight loss curve for the DMEA salt solution. The rates of loss of the various forms of 2,4-D at 120° C. are summarized in Table 7.

TABLE 7

Rates of Loss of Various Forms of 2,4-D

| Form of 2,4-D | Rate of Loss (μg/min) |
|---|---|
| 2,4-D K Half Salt | 0.132 |
| 2,4-D Acid | 2.29 |
| 2,4-D EHE | 11 |
| 2,4-D DMA | 1.5 |
| 2,4-D DMEA | 0.905 |

Example 7

Weed Control Using Synthetic Auxin Half Salts

Methods for Applying 2,4-D Salts and Glufosinate+2,4-D in the Greenhouse

Plant material was propagated in the Indianapolis greenhouses under warm temperature conditions of 26 to 28° C. and a 16 hour day length and 8 hour dark cycle. Natural light was supplemented with 1000-watt metal halide overhead lamps with an average illumination of 500 μE m−2 s−1 photosynthetic active radiation for 16 consecutive hours each day. Seeds of each species were planted in 10 cm square pots containing a potting soil, Metro-Mix 360®. Metro-mix 360® consists of Canadian sphagnum peat moss, coarse perlite, bark ash, a starter nutrient charge (with gypsum), a slow-release nitrogen fertilizer and dolomitic limestone. Plants were top watered prior to treatment and sub-irrigated after treatment. Plant material was fertilized three times a week with Jack's fertilizer solution (Jack's Professional 15-5-15 4 Ca 2 Mg fertilizer manufactured by JR PETERS INC.; 6656 Grant Way; Allentown, Pa. 18106). Appropriate amounts of herbicides were weighed and diluted with Indianapolis tap water.

All treatments were applied to selected plant species with a track sprayer (Generation III Research Sprayer manufactured by DeVries Manufacturing in Hollandale, Minn., USA) located in building 306, laboratory E1-483, at the Dow AgroSciences facility in Indianapolis, Ind. The track sprayer was calibrated to deliver 140 L/ha at 40 psi (262 kPa) pressure utilizing an 8002E even, flat fan nozzle. Track sprayer speed was set at 1.6 mph (2.4 km h−1). Applications were made to replicates of each species in a randomized complete block design, with 4 replications per treatment.

All species were evaluated at 15 or 21 days after application (DAA). The treated plants and control plants were evaluated using a rating scale of 0-100%, wherein 0% indicates no injury or control of the vegetation and 100% indicates complete death of the plants.

TABLE 8

Control of common lambsquarters (CHEAL), sicklepod (CASOB), redroot pigweed (AMARE) and common ragweed (AMBTR) with several forms of 2,4-D with no adjuvant 21 days after application (DAA)

| Treatment | Rate (g ae/ha) | CHEAL | CASOB | AMARE | AMBTR |
|---|---|---|---|---|---|
| | | | % Control | | |
| 2,4-D DMA | 800 | 73 | 95 | 91 | 100 |
| 2,4-D K half-salt | 800 | 84 | 100 | 91 | 100 |
| 2,4-D Na half-salt | 800 | 85 | 100 | 92 | 100 |
| 2,4-D NH4 | 800 | 92 | 100 | 95 | 99 |
| 2,4-D NH4 half-salt | 800 | 74 | 100 | 91 | 100 |
| 2,4-D Choline | 800 | 74 | NT$^a$ | 95 | NT$^a$ |

$^a$Not tested on this species.

TABLE 9

Control of prickly sida (SIDSP), sicklepod (CASOB) and broadleaf signalgrass (BRAPP) with gufosinate + 2,4-D potassium (K) half-salt compared to glufosiante + 2,4-D choline tank-mix 15 days after application (DAA)

| Treatment | Rate (g ae/ha) | SIDSP | CASOB | BRAPP |
|---|---|---|---|---|
| | | | % Control | |
| Glufosinate + 2,4-D K half-salt, Pre-mix | 542 + 1120 | 99 | 100 | 85 |
| Glufosinate + 2,4-D K half-salt, Tank-mix | 542 + 1120 | 99 | 100 | 83 |
| Glufosinate + 2,4-D Choline | 542 + 1120 | 96 | 100 | 85 |
| Glufosinate + 2,4-D K half-salt, Pre-mix | 271 + 560 | 76 | 100 | 65 |
| Glufosinate + 2,4-D K half-salt, Tank-mix | 271 + 560 | 93 | 99 | 60 |
| Glufosinate + 2,4-D Choline | 271 + 560 | 94 | 100 | 60 |
| Glufosinate + 2,4-D K half-salt, Pre-mix | 135 + 280 | 83 | 98 | 3 |
| Glufosinate + 2,4-D K half-salt, Tank-mix | 135 + 280 | 85 | 96 | 8 |
| Glufosinate + 2,4-D Choline | 135 + 280 | 85 | 96 | 10 |

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or steps may be explicitly mentioned herein; however, other combinations of components and steps are included, even though not explicitly stated. The term "comprising" and variations thereof as used herein is used synonymously with the term "including" and variations thereof and are open, non-limiting terms.

What is claimed is:

1. A half salt of a synthetic auxin herbicide that has the formula

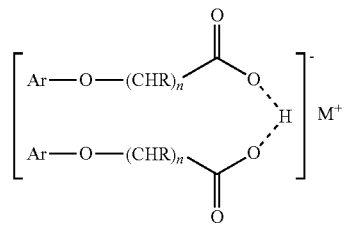

wherein R is independently H or CH$_3$; n is an integer selected from 1, 2 or 3; Ar is a phenyl or pyridine group substituted with one or more substituents selected from halogen, C$_1$-C$_6$ alkyl, C$_1$-C$_6$ haloalkyl, C$_1$-C$_6$ alkoxy, amino, C$_1$-C$_6$ alkylamino, and di(C$_1$-C$_6$ alkyl)amino; and M is a monovalent metal cation or a tetrasubstituted ammonium ion; and wherein the half salt has a water solubility within a pH range of from about 3 to about 6 of less than about 1 wt % with respect to the total weight of water and the half salt.

2. The half salt of claim 1, wherein the monovalent metal cation is selected from the group consisting of lithium, sodium, and potassium.

3. The half salt of claim 1, wherein the tetrasubstituted ammonium ion is selected from the group consisting of tetramethyl ammonium, tetraethyl ammonium and choline.

4. The half salt of claim 1, wherein the synthetic auxin herbicide is selected from the group consisting of 2,4-D, 2,4-DB, triclopyr, fluroxypyr, MCPA, MCPB, mecoprop, and mecoprop-P.

5. The half salt of claim 4 wherein the synthetic auxin herbicide is 2,4-D and M is sodium.

6. The half salt of claim 4 wherein the auxin herbicide is 2,4-D and M is potassium.

7. The half salt of claim 4 wherein the auxin herbicide is 2,4-D and M is lithium.

8. The half salt of claim 4 wherein the auxin herbicide is 2,4-D and M is choline.

9. The half salt of claim 4 wherein the auxin herbicide is triclopyr and M is sodium.

10. The half salt of claim 4 wherein the auxin herbicide is triclopyr and M is potassium.

11. The half salt of claim 4 wherein the auxin herbicide is triclopyr and M is lithium.

12. The half salt of claim 4 wherein the auxin herbicide is triclopyr and M is choline.

13. The half salt of claim 4 wherein the auxin herbicide is fluroxypyr and M is sodium.

14. The half salt of claim 4 wherein the auxin herbicide is fluroxypyr and M is potassium.

15. The half salt of claim 4 wherein the auxin herbicide is fluroxypyr and M is lithium.

16. The half salt of claim 4 wherein the auxin herbicide is fluroxypyr and M is choline.

17. A herbicidal composition comprising the half salt of claim 1.

18. The herbicidal composition of claim 17, further comprising one or more agriculturally acceptable adjuvants or carriers.

19. The herbicidal composition of claim 17, wherein the composition is a liquid concentrate or a dry concentrate.

20. The herbicidal composition of claim 19, wherein the liquid concentrate is a suspension concentrate.

21. The herbicidal composition of claim 19, wherein the dry concentrate is selected from the group consisting of a powder, a granule, and a dispersible granule.

22. The herbicidal composition of claim 17, wherein the composition is an aqueous spray solution or mixture.

23. The herbicidal composition of claim 17 further comprising a second herbicide.

24. The herbicidal composition of claim 23, wherein the second herbicide is selected from the group consisting of glyphosate, glufosinate, and salts thereof.

25. The composition of claim 17, wherein the synthetic auxin comprises the sodium half salt of 2,4-D and a salt of glyphosate.

26. The composition of claim 17, wherein the synthetic auxin comprises the potassium half salt of 2,4-D and a salt of glyphosate.

27. The composition of claim 17, wherein the synthetic auxin comprises the lithium half salt of 2,4-D and a salt of glyphosate.

28. The composition of claim 17, wherein the synthetic auxin comprises the choline half salt of 2,4-D and a salt of glyphosate.

29. The composition of claim 17, wherein the synthetic auxin comprises the sodium half salt of 2,4-D and a salt of glufosinate.

30. The composition of claim 17, wherein the synthetic auxin comprises the potassium half salt of 2,4-D and a salt of glufosinate.

31. The composition of claim 17, wherein the synthetic auxin comprises the lithium half salt of 2,4-D and a salt of glufosinate.

32. The composition of claim 17, wherein the synthetic auxin comprises the choline half salt of 2,4-D and a salt of glufosinate.

33. The composition of claim 25, wherein the salt of glyphosate is selected from the group consisting of the isopropyl ammonium salt, the dimethyl ammonium salt, and the potassium salt.

34. The composition of claim 26, wherein the salt of glyphosate is selected from the group consisting of the isopropyl ammonium salt, the dimethyl ammonium salt, and the potassium salt.

35. The composition of claim 27, wherein the salt of glyphosate is selected from the group consisting of the isopropyl ammonium salt, the dimethyl ammonium salt, and the potassium salt.

36. The composition of claim 28, wherein the salt of glyphosate is selected from the group consisting of the isopropyl ammonium salt, the dimethyl ammonium salt, and the potassium salt.

37. The composition of claim 29, wherein the salt of glufosinate is the ammonium salt.

38. The composition of claim 30, wherein the salt of glufosinate is the ammonium salt.

39. The composition of claim 31, wherein the salt of glufosinate is the ammonium salt.

40. The composition of claim 32, wherein the salt of glufosinate is the ammonium salt.

41. A method of preparing the half salt of claim 1 comprising:
  a) combining:
   i) a solution consisting essentially of a first solvent and a synthetic auxin herbicide of formula

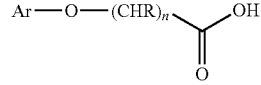

wherein R is independently H or $CH_3$; n is an integer selected from 1, 2 or 3; Ar is a phenyl or pyridine group substituted with one or more substituents selected from halogen, $C_1$-$C_6$ alkyl, $C_1$-$C_6$ haloalkyl, $C_1$-$C_6$ alkoxy, amino, $C_1$-$C_6$ alkylamino, and di($C_1$-$C_6$ alkyl)amino; and
   ii) a solution consisting essentially of a second solvent and one half molar equivalent of a base selected from the group consisting of sodium hydroxide, potassium hydroxide, lithium hydroxide, tetramethylammonium hydroxide, tetraethylammonium hydroxide and choline hydroxide; and
  b) reacting the synthetic auxin herbicide and the base in the combined first and second solvents.

42. The method of claim 41, wherein the synthetic auxin herbicide is selected from the group consisting of 2,4-D, 2,4-DB, triclopyr, fluroxypyr, MCPA, MCPB, mecoprop, and mecoprop-P.

43. A method of controlling undesirable vegetation comprising contacting the vegetation or a locus thereof with, or applying to soil to prevent the emergence of vegetation, a herbicidally effective amount of the herbicidal composition of claim 17.

* * * * *